(12) United States Patent
Giralt Lledó et al.

(10) Patent No.: US 8,008,492 B2
(45) Date of Patent: Aug. 30, 2011

(54) COMPOUNDS THAT ACT AS A VEHICLE FOR DELIVERY THROUGH THE BLOOD-BRAIN BARRIER AND CHARGE DELIVERY VEHICLE CONSTRUCTIONS

(76) Inventors: Ernest Giralt Lledó, Sant Just Desvern (ES); Meritxell Teixidó Turà, Sant Joan Despí (ES)

(*) Notice: Subject to any disclaimer, the term of this patent is extended or adjusted under 35 U.S.C. 154(b) by 0 days.

(21) Appl. No.: 12/439,490

(22) PCT Filed: Aug. 28, 2007

(86) PCT No.: PCT/ES2007/000499
§ 371 (c)(1),
(2), (4) Date: Mar. 2, 2009

(87) PCT Pub. No.: WO2008/025867
PCT Pub. Date: Mar. 6, 2008

(65) Prior Publication Data
US 2010/0010011 A1    Jan. 14, 2010

(30) Foreign Application Priority Data
Sep. 1, 2006 (ES) .................................. 200602296

(51) Int. Cl.
C07D 241/04 (2006.01)
C07D 295/00 (2006.01)
(52) U.S. Cl. ....................................................... 544/387
(58) Field of Classification Search .................... 544/387
See application file for complete search history.

(56) References Cited

FOREIGN PATENT DOCUMENTS
EP         0614886 A1   9/1994
WO    W02005054279 A1   6/2005

OTHER PUBLICATIONS

Gyore J and Ecet M, "Thermal behavior of phenylalanine and aminophenylalanine," Thermal Analysis, Proceedings of the 4th International Conference, 1975, 2, 387-394.*
King, F.D. (Ed.), "Bioisosteres, conformational restriction and prodrugs—case history: an example of a conformational restriction approach," Medical Chemistry: Principles and Practice, 1994, Chapter 14, 206-209.*
Vippagunta SR, Brittain HG, and Grant D J, "Crystalline solids," Advanced Drug Delivery Reviews, May 2001,48(1), 3-26.*
Fortin, David et al., Enhanced Chemotherapy Delivery by Intraarterial Infusion and Blood-Brain Barrier Disruption in Malignant Brain Tumors, Wiley InterScience (http://www.interscience.wiley.com), May 4, 2005, pp. 2606-2615, American Cancer Society.
Stewart, John M. et al., The Chemistry of Solid Phase Peptide Synthesis, Solid Phase Peptide Synthesis Second Edition, 1984, pp. 1-8, Pierce Chemical Company.
Atherton, E. et al., Solid Phase Synthesis—the Merrifield Technique, Solid Phase Peptide Synthesis, A Practical Approach, pp. 13-23, IRL Press at Oxford University Press, 1989.
Lloyd-Williams, Paul et al., Introduction, Chemical Approaches to the Synthesis of Peptites and Proteins, 1997, pp. 1-16, CRC Press Inc., Boca Raton, Florida, USA.
Biron, Eric et al, Optimized Selective N-Methylation of Peptides on Solid Support, J. of Peptide Sci., 2006, pp. 213-219, vol. 12, European Peptide Society and John Wiley & Sons, Ltd.
Yang, Lihu. et al., Solid Phase Synthesis of Fmoc N-Methyl Amino Acids: Application of the Fukuyama Amine Synthesis, Tetrahedron Letters, 1997, pp. 7307-7310, vol. 38, No. 42, Elsevier Science Ltd.
Greene, Theodora W. et al., Protection for the Amino Group, Protective Groups in Organic Synthesis Third Edition, 1999, pp. 318-319, 327-330, John Wiley & Sons, Inc.
Kaiser, E. et al., Color Test for Detection of Free Terminal Amino Groups in the Solid-Phase Synthesis of Peptides, Analytical Biochemistry, An International Journal, 1970, pp. 595-598, vol. 34, Academic Press.
Madder, Annemieke et al., A Novel Sensitive Colorimetric Assay for Visual Detection of Solid-Phase Bound Amines, Eur. J. Org. Chem, 1999, pp. 2787-2791, Wiley-VCH Verlag GmbH.
Teixido, Meritxell et al., Evolutionary Combinatoral Chemistry, a Novel Tool for SAR Studies on Peptide Transport Across the Blood-Brain Barrier, Part 2. Design, Synthesis and Evaluation of a First Generation of Peptides, J. Peptide Sci, 2005, pp. 789-804, vol. 11, European Peptide Society and John Wiley & Sons, Ltd.
International Search Report for International Application No. PCT/ES2007/000499, Nov. 1, 2008.

* cited by examiner

*Primary Examiner* — San-Ming Hui
*Assistant Examiner* — Paul Zarek
(74) *Attorney, Agent, or Firm* — Peter B. Scull; K Kalan; Berenbaum Weinshienk PC

(57) ABSTRACT

Compounds of formula (I), where $R_1$ and $R_3$ are H or ($C_1$-$C_4$)-alkyl; $R_2$ is H or a C-radical derived from one of the known ring systems with 1-4 rings; $X_1$ is a ($C_1$-$C_6$)-alkyl biradical derived from a linear or branched carbon chain; and $X_2$ is —NH—, —NH—$(CH_2)_{1-3}$—COO—, —NH—$(CH_2)_{1-3}$—S—, or —NH—CO—$(CH_2)_{1-3}$—S—, are useful as blood-brain barrier shuttles (BBB). BBB shuttle-cargo constructs, the cargo being a substance susceptible to form an amide or an ester or a disulfide bound with $X_2$ and being unable to cross the blood-brain barrier by itself, are useful as medicaments.

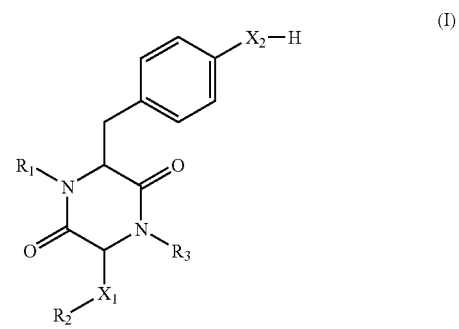

(I)

9 Claims, No Drawings

COMPOUNDS THAT ACT AS A VEHICLE FOR DELIVERY THROUGH THE BLOOD-BRAIN BARRIER AND CHARGE DELIVERY VEHICLE CONSTRUCTIONS

This invention relates to the fields of medicine, research and diagnostics, and more specifically to new compounds that act as blood-brain barrier (BBB) shuttles for the delivery of substances that cannot cross the BBB by themselves. It also relates to BBB shuttle-cargo constructs and to their use as a medicament.

BACKGROUND ART

Many of the current major therapeutic problems require treatment of the brain. This includes neurodegenerative diseases such as Parkinson and Alzheimer diseases, but also central nervous system diseases such as schizophrenia, epilepsy and bipolar disorder. Also brain cancer, human immunodeficiency virus (HIV) and even certain aspects of obesity as pharmaceutical targets located inside the brain can be included. In many cases there are promising compounds for their treatment, however owing to their BBB transport problems more than 98% of these potential drugs do not go to development stage.

The BBB is a natural filter within the body that only allows certain substances through from the blood to the brain. It is a natural defense mechanism designed to keep harmful substances out of the brain. It controls the composition of the brain extracellular fluid independent of fluctuations within the blood. It is also impermeable for many environmental compounds and drugs.

The anatomical basis of the BBB is primarily the tight junction at endothelial cells of cerebral microvessels. Cerebral microvessels form a continuous membrane with no fenestrations and the tight junctions between them are responsible for a high transendothelial electrical resistance. Specific transporters mediate the access of certain molecules important for the brain, such as glucose, isolated amino acids and ions. Other compounds or drugs are dependent on diffusion through the lipid bilayers of the endothelial membranes which requires a certain degree of lipophilicity of these compounds.

There are different therapeutical fields where there is a need to find new drugs that can cross the BBB to arrive to its target site. For instance, the brain might serve as an occult reservoir for human immunodeficiency virus (HIV) viral replication. HIV in the brain and in the cerebro-spinal fluid may be particularly resistant to chemotherapy because of the failure of anti-retroviral drugs to penetrate the BBB. The virus can cross the BBB either during primary infection or at a later stage. The resulting infection leads to a number of central-nervous system disorders such as acquired immunodeficiency syndrome (AIDS) dementia complex and HIV encephalopathy.

Brain cancer can be counted among the most deadly and intractable diseases. Presently the treatment of brain cancer consist on surgery, radiation therapy using high-energy X-rays or other types of radiation and chemotherapy using anti-cancer or cytotoxic drugs. These anticancer drugs can reach cancer cells wherever they are in the body, but in the case of brain tumors not all chemotherapy drugs are suitable, because most of them cannot cross the blood-brain barrier (cf. D. Fortin et al., "Enhanced chemotherapy delivery by intraarterial infusion and blood brain barrier disruption in malignant brain tumors", Cancer 2005, vol. 103, pp. 2606-15).

Another field of interest is psychiatric diseases, such as schizophrenia. Schizophrenia affects about 1% of the population. Although anti-psychotic drugs are been used, there is a need to find new and better drugs without the undesired side effects of the existing ones. In the search of these novels drugs the BBB is the barrier that the drug will need to cross to arrive to its target site.

Another field of interest is neurodegenerative diseases, such as Parkinson disease. Parkinson's disease is one of the major neurodegenerative disorders, affecting 3% of the population over the age of 65. Currently there is no preventive therapy for Parkinson's disease. The actual treatment consist of improving the motor symptoms by supplementation of the deficient neurotransmitter dopamine. As dopamine does not cross the BBB, a precursor of dopamine, L-dopa, has been used in the treatment of Parkinson disease since the 1960's. However, severe side effects are frequently observed within a few years of L-dopa therapy. L-dopa crosses the BBB using an amino acid transporter and once inside it is transformed to dopamine by the aromatic L-amino acid descarboxylase.

Finally, another field of interest is epilepsy, a syndrome of episodic brain dysfunction that affects about 1% of the general population. About 30% of epilepsies are classified as symptomatic since they are associated with an identifiable central nervous system injury, while the rest of them do not have identified causes. Current medical therapy of epilepsy is largely symptomatic and it is aimed at controlling seizures in affected individuals. If antiepileptic drugs fail, a temporal lobectomy, an operation which involves removing the region of the brain from which the seizures originates, provides an alternative treatment. This operation is highly successful in most cases, but fails in some, and moreover many individuals are reluctant to undergo surgery that involves removing parts of the brain.

In all these cases, many promising compounds are known for their treatment, however, owing to their BBB transport problems, they are not further developed. Research in these fields have taken several approaches. Some methods of administration of drugs to the brain either for therapy or diagnosis are invasive techniques, such as intracranial administration, administration altering BBB integrity or osmotic disruption. Other methods of administration of drugs to the brain have undesired side effects derived from the administration at high doses.

Another approach is drug modification. These modifications include for instance reduction of drug size or increase of drug lipophylicity, but it is not always possible to introduce such modifications. In the case of introducing an irreversible modification it is necessary that it does not alter the drug activity once it gets to the target site. In the case of a bioreversible modification, it is necessary to find an enzymatic or chemical process that will recover the active drug once the prodrug is inside the central nervous system.

Another approach is the administration by conjugation to a biological carrier. This strategy use monoclonal antibodies that bind to the transferrin receptor and undergo receptor mediated endocytosis, as molecular trojan horses of compounds with a therapeutical use that can not cross the BBB by themselves.

Thus despite all the research efforts invested in the past, there is still an important need to find substances having pharmacologically or diagnostic utility that can cross the BBB.

SUMMARY OF THE INVENTION

Inventors provide new compounds, referred to as "shuttle" compounds, which have the ability to cross the BBB and which are able to enter into the brain drugs or other substances such as diagnostic agents, referred to as "cargoes", that cannot cross the BBB by themselves. The shuttle compounds are biodegradable and biocompatible, lack intrinsic toxicity and antigenicity as they are made of amino acids.

Thus, a first aspect of the present invention refers to the provision of shuttle compounds of formula (I), or pharmaceutically acceptable salts thereof, or solvates thereof, including stereoisomers or mixtures of stereoisomers,

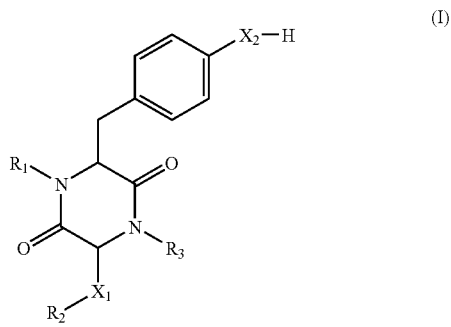

(I)

where: $R_1$ and $R_3$ are radicals independently selected from H and $(C_1$-$C_4)$-alkyl; $R_2$ is H or a C-radical derived from one of the known ring systems with 1-4 rings; the rings being saturated, partially unsaturated or aromatic; the rings being isolated or partially/totally fused and having 5-6 members; each member being independently selected from C, CH, $CH_2$, N, NH, O, and S; the hydrogen atoms of these members being optionally substituted by substituents selected from $(C_1$-$C_6)$-alkyl and $(C_1$-$C_6)$-alkoxy; $X_1$ is a $(C_1$-$C_8)$-alkyl biradical derived from a linear or branched carbon chain; and $X_2$ is a biradical selected from —NH—, —NH—$(CH_2)_{1-3}$—COO—, —NH—$(CH_2)_{1-3}$—S—, and —NH—CO—$(CH_2)_{1-3}$—S—.

Preferred compounds are those of formula (I) where the members of the ring in $R_2$ are C, CH, or $CH_2$. More preferred compounds are those where $X_1$ is —$CH_2$— and $R_2$ is phenyl, cyclohexyl, 2-naphtyl, or 1-pyrenyl, or those compounds where $X_1$ is n-hexyl and $R_2$ is H. Specially preferred are those compounds where $R_1$ and/or $R_3$ are methyl. All these compounds can be prepared from N-methyl amino acids that will increase the half life of our constructs in the body, avoiding the degradation by different peptidases in the blood or associated with cerebral microvessels.

The most preferred compounds are the following: the of formula (I) with $R_1$=H; $R_2$=phenyl, $X_1$=$CH_2$, $R_3$=$CH_3$, and $X_2$=NH; the compound of formula (I) with $R_1$=$CH_3$; $R_2$=phenyl, $X_1$=$CH_2$, $R_3$=$CH_3$, and $X_2$=NH; and the compound of formula (I) with $R_1$=H; $R_2$=phenyl, $X_1$=$CH_2$, $R_3$=$CH_3$, and $X_2$=—NH—$(CH_2)$—COO—. These three compounds can also be referred to as DKP Phe (ρ-$NH_2$)—N-MePhe, DKP N-MePhe-N-MePhe(ρ-$NH_2$), and DKP Phe(ρ-NH—$CH_2$—COOH)—N-MePhe respectively, DKP stating for diketopiperazine.

Compounds of formula (I) have the capability to transport into the brain substances, referred to as cargoes, that cannot cross the BBB by themselves. Thus, another aspect of the invention refers to the use of compounds of formula (I) as BBB-shuttles. The use of these compounds make it possible for instance that the research of novel drugs is not only limited to the compounds that can cross the BBB by themselves.

The BBB transport mechanism of the compounds of formula (I) is passive diffusion and this mechanism is independent of the L or D configuration of the amino acids. Thus, one of the main advantages of the compounds of formula (I) is that they can be prepared from L or D amino acids, or even from racemic mixtures.

The compounds of formula (I) have appropriate functional groups for covalent fixation of cargoes maintaining the original activity of the cargo, until it reaches the site of action. Thus, another aspect of the present invention is the provision of constructs of formula (II), referred to as BBB shuttle-cargo constructs,

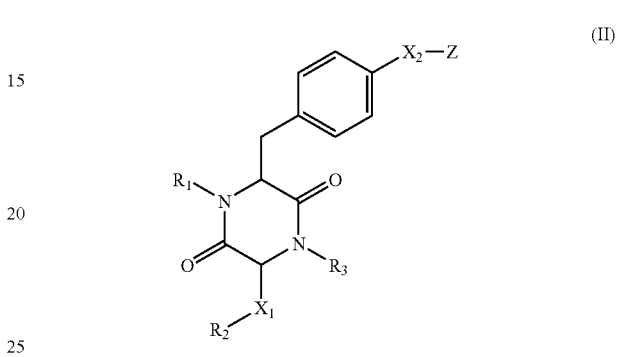

(II)

where $R_1$, $R_2$, $R_3$, $X_1$ and $X_2$ are as defined above, including the mentioned preferences; and Z is a radical derived from a substance susceptible to form an amide or an ester or a disulfide bond with $X_2$, said substance being unable to cross the blood brain barrier by itself. Substances from which radical Z is derived include a wide range of substances having pharmacologically or diagnostic utility. These substances can be active pharmaceutical ingredients, in particular antiretroviral agents, anticancer agents, anti-psychotic agents, antineurodegenerative agents or antiepyleptic agents. Examples of active pharmaceutical ingredients are dopamine or baicalin. Dopamine is a key neurotransmitter in the central nervous system, in particular striatal dopamine depletion is associated with clinical conditions of parkinsonism. Baicalin, is a flavonoid non-nucleoside reverse transcriptase inhibitor (NNRTI), isolated from the traditional Chinese medicinal plant *Scutellaria Baicalensis Georgi*. Both compounds show interesting properties but they cannot cross the BBB. In particular, as illustrated in the examples, the constructs of formula (II) allow that either dopamine or baicalin have a future in their way to become commercial drugs, avoiding the undesired side effects of the actual therapy, and being a simpler and none invasive technique compared with the existing ones.

Substances from which Z is derived also include other substances that would be interesting to transport to the brain but they cannot do it properly alone, for example contrast agents for Magnetic Resonance Imaging (MRI). Among clinical devices used for cancer diagnosis, MRI outstands as a non-invasive and non-destructive powerful imaging modality that provides internal images of living organisms with no limits in the depth of analysis and with a resolution of 10-100 μm. It is a very valuable technique widely used in cancer diagnosis and research. To perform MRI contrast agents are needed. Contrast agents can be used as a diagnostic method for central nervous system diseases such as Alzheimer disease or brain cancer, or as a tool for pre-operative MRI scan that will guide the surgeon. In all these cases the contrast agent used needs to cross the BBB. Example of contrast agents include magnetic nanoparticles such as superparamagnetic iron oxide nanoparticles. Other diagnostic agents include fluorescent dyes or probes such as carboxyfluorescein and derivatives, lucifer yellow, rhodamine or texas red.

Shuttle compounds of formula (I) may be formed by natural and non-natural amino acids and/or their derivatives. Compounds of formula (I) and the shuttle-cargo constructs of formula (II) may be generated wholly or partly by chemical synthesis. Suitable amino acids for the preparation of compounds of formula (I) are commercially available. Compounds of formula (I) and the constructs of formula (II) can be readily prepared, for example, according to well-established, standard liquid or, preferably, solid-phase peptide synthesis methods, general descriptions of which are broadly available (cf. e.g. J. M. Stewart et al., "Solid Phase Peptide Synthesis", 2nd edition, Pierce Chemical Company, Rockford, Ill. 1984; E. Atherton et al., "Solid Phase Peptide Synthesis, A Practical Approach", IRL Press 1989; and P. Lloyd-Williams et al., "Chemical Approaches to the Synthesis of Peptides and Proteins", CRC Press Inc, Boca Raton, Fla., USA, 1997); or they may be prepared in solution, or by any combination of solid-phase, liquid phase and solution chemistry. For instance, by first completing the BBB-shuttle portion and then after removal of any present protecting groups, by introduction of the cargo in solution.

The compounds of formula (I) where $R_1$ and/or $R_3$ are methyl may be prepared from N-methyl amino acids. The N-methyl amino acids used can be incorporated using commercially available building blocks or via N-methylation on solid-phase using the corresponding non N-methylated amino acid. The N-methylation of the amino acid derivatives can be performed using described methods (cf. Biron et al., *Science* 2006, vol. 12, pp. 213-219; Yang et al., *Tetrahedron Letters*, 1997, vol. 38, pp. 7307-7310). The N-alkylation of the amino acids attached to the resin can be done in three steps: (a) protection and activation with o-nitrobenzenesulfonyl chloride (O-NBS); (b) Mitsunobu reaction and (c) O-NBS removal. Suitable protecting groups necessary during the BBB-shuttles synthesis are well-known in the art (cf. e.g., Greene et al., "Protective Groups in Organic Synthesis", 2nd ed., 1991 John Wiley & Sons, Inc. Somerset, N.J.) and include 9-fluorenylmethoxycarbonyl (Fmoc), and t-butoxycarbonyl (Boc).

Another aspect of the invention refers to pharmaceutical compositions comprising a therapeutically effective amount of the shuttle-cargo constructs of formula (II) together with appropriate amounts of pharmaceutical excipients or carriers. The person skilled in the art will choose the appropriate administration via by usual methods. The amount of the construct to be administered, rate and time-course of administration, will depend on the nature and severity of what is being treated. The precise nature of the carrier or other excipients will depend on the route of administration, which may be oral, nasal or by injection, e.g. cutaneous, subcutaneous or intravenous.

A composition comprising a construct according to the present invention may be administered alone or in combination with other treatments, either simultaneously or sequentially depending upon the condition to be treated. Another aspect of the present invention refers to the constructs of the present invention for use as a medicament. In particular, the invention also refers to the use of the constructs of formula (II) where Z is a radical from dopamine for the preparation of a medicament for the treatment of Parkinson's disease. Therefore, the invention is related to a method of treatment and/or prophylaxis of a mammal, including a human, suffering from or being susceptible to Parkinson's disease, the method comprising the administration to said patient of a therapeutically effective amount of a compound of formula (II) with Z derived from dopamine, together with pharmaceutically acceptable diluents or carriers.

The invention also refers to the use of the constructs of formula (II) where Z is derived from baicalin for the preparation of a medicament for the treatment of AIDS dementia complex or HIV encephalopathy. Therefore, the invention is related to a method of treatment and/or prophylaxis of a mammal, including a human, suffering from or being susceptible AIDS dementia complex or HIV encephalopathy, said method comprising the administration to said patient of a therapeutically effective amount of a compound of formula (II) with Z derived from baicalin, together with pharmaceutically acceptable diluents or carriers.

Additional objects, advantages and features of the invention will become apparent to those skilled in the art upon examination of the description or may be learned by practice of the invention. Throughout the description and claims the word "comprise" and variations of the word, are not intended to exclude other technical features, additives, components, or steps. The disclosure in the abstract of this application is incorporated herein as reference. The following examples and drawings are provided by way of illustration, and they are not intended to be limiting of the present invention.

DETAILED DESCRIPTION OF PARTICULAR EMBODIMENTS

Protected amino acids, handles and resins were supplied by: Luxembourg Industries (Tel-Aviv, Israel), Neosystem (Strasbourg, France), Calbiochem-Novabiochem AG (Laüfelfingen, Switzerland), Bachem AG (Bubendorf, Switzerland) o Iris Biotech (Marktredwitz, Germany). Other reagents and solvents used are summarized in Table 1.

TABLE 1

Comercials suppliers and reagents used. DCM passed through a $Al_2O_3$ column. DMF is stored on molecular sieves 4 Å and nitrogen is bubbled in order to eliminate volatile agents.

| Commercial supplier | Reagents and solvents |
|---|---|
| Albatros Chem. Inc. Aldrich | N-hydroxybenzotriazole (HOBt) 4-Bromomethyl-3-nitrobenzoic acid, dopamine, L-dopa, baicalin, phenol, piperidine, triphenylphosphine, 2,5-dihydroxibenzoic acid (DHB), α-ciano-4-hydroxicinnamic acid (ACH), DOWEX MR-3 Mixed Bed, dispers red I, ethyl diazoacetate, 1,8-diazabicyclo-[5.4.0]-undec-7-ene (DBU), $NaBH_3CN$, glyoxilic acid, o-nitrobenzenesulfonyl chloride (O-NBS), collidine, diisopropyl azodicarboxylate (DIAD), citric acid |

TABLE 1-continued

Comercials suppliers and reagents used. DCM passed through a
$Al_2O_3$ column. DMF is stored on molecular sieves 4 Å and nitrogen is bubbled
in order to eliminate volatile agents.

| Commercial supplier | Reagents and solvents |
| --- | --- |
| Applied Biosystems | (7-Azabenzotriazol-1-yloxy)tripyrrolidinophosphonium hexafluorophosphate (PyAOP) |
| Applied GL Biochem Shangai | 1-Hydroxy-7-azabenzotriazole (HOAt) |
| Avantis | Porcine polar brain lipid extract (PBLEP) |
| Cambridge Isotope Laboratories Inc. | $CD_3OD$, $CDCl_3$ |
| Fluka | N,N-Diisopropylethylamina (DIEA), diethylamina (DEA), N,N'-diisopropylcarbodiimide (DIPCDI), 4-dimethylaminopiridine (DMAP), KCN, $KHSO_4$, ninhidrine, β-mercaptoethanol |
| Jescuder | NaOH |
| KaliChemie | Trifluoroacetic acid (TFA) |
| Merck | Molecular sieves 4 Å, Thin layer chromatography layers (TLC) |
| Millipore | Polyvinylidine diFluoride (PVDF) filters 0.45 μm |
| Novabiochem | Benzotriazol-1-yl-oxytripyrrolidinophosphonium hexafluorophosphate (PyBOP) |
| Panreac | Dimethyl sulfoxide (DMSO), $MgSO_4$, $P_2O_5$ |
| pION | PAMPA plates, PAMPA system solution |
| Scharlau | AcOH, dichloromethane (DCM)*, dimethylformamide (DMF)**, EtOH absolute, MeOH, tert-butylmethylether (TBME), HCl, piridine, N-methyl pyrrolidone (NMP), AcOEt |
| SDS | Acetone, MeCN, THF, chloroform, toluene |
| Sigma | $K_2CO_3$, NaCl, $NaHCO_3$, $NaH_2PO_4$, $Na_2HPO_4$, Phosphate Buffered Saline (PBS) |

General considerations about the synthesis. Solid-phase peptide elongation and other solid-phase manipulations were carried out manually in polypropylene syringes fitted with a polyethylene porous disk. Solvents and soluble reagents were removed by suction. Washings between different synthetical steps were carried out with dimethylformamide (DMF) (5×0.5 min) and dichloromethane (DCM) (5×0.5 min) using 10 mL of solvent/g of resin each time.

Identification tests. The test used for the identification and control of the synthesis were the following: A) Kaiser calorimetric assay for the detection of solid-phase bound primary amines (cf: E. Kaiser et al., "Color test for detection of free terminal amino groups in the solid-phase synthesis of peptides"; *Anal. Biochem.* 1970, vol. 34, pp. 595-598); B) De Clercq test for secondary amines bound to solid-phase (cf. A. Madder et al., "A novel sensitive calorimetric assay for visual detection of solid-phase bound amines". *Eur. J. Org. Chem.* 1999, pp. 2787-2791). The De Clercq assay is performed by first washing a small sample of the resin (aprox. 1 mg) with DMF (4×1 minutes) and DCM (4×1 minutes). To the resin is added ten drops of reagent solution (0.002 M p-nitrophenyl ester of disperse red 1 in MeCN) and the resulting mixture is heated at 70° C. for 10 minutes. The solution is then decanted and the resin washed with DMF until a transparent supernatant is obtained. The presence of secondary amines is indicated by red colored resin beads.

Protocols used during the synthesis of the constructs of formula (I): they were synthesized on a 100 μmol scale using the following methods and protocols;

Resin initial conditioning. The syntheses start with the conditioning of the resin 4-methylbenzilhydrilamine (ρ-MBHA). This is done washing the resin 5 times with dichloromethane (DCM) for 30 seconds each time followed of a washing with a trifluoroacetic acid solution (TFA) 40% in DCM (1×30 s+2×5 min). This acid treatment is followed by a neutralization step with N,N-diisopropylethylamine (DIEA) 5% in DCM (3×2 min) and finally washing the resin 5 times with DCM for 30 seconds each.

Synthesis of 4-hydroxymethyl-3-nitrobenzoic acid (Nbb handle). In a round-bottom flask provided with reflux system, 4.5 g (17.3 mmols) of 4-bromomethyl-3-nitrobenzoic acid were placed, and an aqueous $NaHCO_3$ saturated solution is added (135 mL). The reaction was stirred and allowed to stand at 90-95° C. The progress of the reaction was monitored by thin layer chromatography (TLC) (chloroform/MeOH/AcOEt, 100:50:0.1, v/v) or by HPLC of an acidified aliquot in a linear gradient 0-100% MeCN in 15 minutes in a Symmetry $C_{18}$ column (150×4.6 mm×5 μm, 100 Å, Waters) retention time for the final product: 7.12 min; retention time for the initial product: 10.39 min. The reaction was completed in 30 minutes. The solution obtained was hot filtered and the reaction was quenched with HCl (12N) to a pH between 1-2 and was extracted with AcOEt (3×100 mL), the different organic fractions were combined, washed with a satured NaCl aqueous solution and dried over $MgSO_4$ anh. The AcOEt was evaporated in vacuo. The product was obtained as a pale yellow solid in a 80% yield. The product has been characterized by HPLC ($t_r$) 7.12 min (linear gradient 0-100% in 15 minutes), HPLC-MS (196 Da) and $R_f$=0.3 by TLC (Chloroform/MeOH/AcOEt, 100:50:0.1, v/v), NMR-$^1$H 400 MHz in $CD_3OD$: Signals: 2H: singlet 4.98 ppm, 1H: doublet, 7.96 ppm (J: 21 Hz), 1H: doublet of doublets, 8.26 ppm (4 Hz, 20 Hz), 1H: doublet, 8.56 ppm (4 Hz).

Coupling of 4-hydroxymethyl-3-nitrobenzoic acid (Nbb handle) to a ρ-MBHA resin. The handle Nbb was attached to the p-MBHA resin using 5 equivalents of Nbb dissolved in DCM and 5 equivalents of N,N'-diisopropylcarbodiimide (DIPCDI) as coupling reagent. The mixture was allowed to react overnight. The solvent was then removed by suction, the resin was thoroughly washed and the reaction was monitored with Kaiser test.

Boc group removal. Removal of the tert-butoxycarbonyl (Boc) protecting group was done with 40% (v/v) TFA in DCM using 2 treatments of 10 minutes each.

Fmoc group removal. Removal of the 9-fluorenylmethyloxycarbonyl (Fmoc) protecting group was done with 20% (v/v) piperidine in DMF using 2 treatments of 10 minutes each.

Coupling Methods:

Coupling of the first aminoacid onto the Nbb handle. For the coupling of the first amino acid to the resin already modified with the handle the following protocol was used: amino acid derivative (4 equiv.), N,N'-diisopropylcarbodiimide (DIPCDI) (4 equiv.) and dimethylaminopiridine (DMAP) (0.4 equiv.) dissolved in DCM (1-3 ml/g resin) were sequentially added to the resin. The mixture was allowed to react with intermittent manual stirring for 30 min. The solvent was then removed by suction, the resin was thoroughly washed and the coupling is repeated once.

Coupling of the second aminoacid. The protected aminoacid derivative was coupled to the first aminoacid already anchored to the resin using the following protocol: Protected amino acid (5 equiv.) in DMF (1-3 mL/g resin) and (7-azabenzotriazol-1-yloxy)tripyrrolidinophosphonium hexafluorophosphate (PyAOP) (5 equiv.) were sequentially added to the resin followed with 15 equiv. of N,N-diisopropylethylamine (DIEA). The mixture was left to react with intermittent manual stirring for 1 h. The solvent was removed by filtration, the resin washed as indicated above, and the coupling was repeated 2 times more. The extent of the coupling was checked by the De Clercq test.

Amino acid N-alkylation. This process can be divided in three steps:

(a) Protection and activation with o-nitrobenzenesulfonyl chloride (O-NBS): To perform the protection 4 equiv. O-NBS and 10 equiv. of collidine in N-methyl pyrrolidone (NMP) were added to the resin. The reaction was left with intermittent manual stirring for 1 h and this step was repeated once and checked by Kaiser test.

(b) Mitsunobu reaction: The Mitsunobu reagents, 5 equiv. triphenylphosphine and 10 equiv. of MeOH in dry THF were added to the resin and left for 1 minute, afterwards without filtering 5 equiv. of diisopropyl azodicarboxylate (DIAD) were added in dry THF and left for another 10 minutes.

(c) O-NBS removal: To proceed to the O-NBS removal 10 equiv. of β-mercaptoethanol and 5 equiv. of 1,8-diazabicyclo-[5.4.0]-undec-7-ene (DBU) in NMP are added to the resin and the mixture was left to react for 5 minutes under argon atmosphere. This process was repeated once.

Introduction of the anchoring moiety: it depends on the nature of the moiety. For instance, the moiety can be introduced by reductive amination adding 5 equiv. of glyoxylic acid (H—CO—COOH) in DMF with 1% AcOH to the resin and leaving it for 30 min. The solvent and reagents were removed by filtration, the resin washed and then 3 equiv. of $NaBH_3CN$ in DMF with 1% AcOH were added to perform the reduction during 1 h.

Coupling of the cargo. Depending on the nature of the cargo, it will be linked to the BBB-shuttle through different types of chemical bonds.

For cargoes with a COOH moiety (e.g. baicalin): The corresponding BBB-shuttle provided with a $NH_2$ group was used and was reacted with 5 equiv. of Cargo-COOH, using 5 equiv. Benzotriazol-1-yl-oxytripyrrolidinophosphonium hexafluorophosphate (PyBOP) and 15 equiv. 1-hydroxy-7-azabenzotriazole (HOAt) as coupling reagents and 15 equiv. of N,N-diisopropylethylamine (DIEA) as a base in DMF during 2 h.

For cargoes with an amine or alcohol moiety (e.g. dopamine): This reaction was done in two steps: first the carboxylic group was activated with 5 equiv. of N,N'-diisopropylcarbodiimide (DIPCDI) and 5 equiv. of HOAt in DMF for 30 min, after which the solvent was removed by suction and the resin was washed. The coupling was performed using 5 equiv. $NH_2$-Cargo in DMF. The mixture was left to react with intermittent manual stirring overnight. The solvent was removed by filtration, the resin was washed.

Neutralization-cyclization and cleavage in one step: It was carried out by treatment of the resin with DIEA 10% in DCM (3×10 minutes). The filtering was collected and DCM evaporated under $N_2$. The residue was dissolved in $H_2O$:MeCN (1:1) and liophilized.

The identity of the different compounds synthesized was confirmed using Matrix Assisted Laser Desorption/Ionization-Mass Spectrometry (MALDI) (Instrument: MALDI Voyager DE RP time-of-flight (TOF) PE Biosystem) or HPLC-MS (Instrument: Waters model Alliance 2796, quaternary pump, UV/Vis detector model 2487, ESI-MS model Micromass ZQ and software Masslynx version 4.0) using a Symmetry 300 $C_{18}$ (150×3.9 mm×5 µm), 300 Å column. 1 mL/min flow, solvents: A: $H_2O$ with 0.1% formic acid; B: MeCN with 0.07% formic acid. Their purity was checked by reverse phase HPLC using a Symmetry $C_{18}$ column (150×4.6 mm×5 µm, 100 Å, Waters), 1 mL/min flow, solvents: A: $H_2O$ with 0.045% TFA; B: MeCN with 0.036% TFA, Instrument: Waters model Alliance 2695 constituted by a quaternary pump, a diode array detector model 966, controlled by the software Millenium version 3.5.

Compounds were purified if necessary by reverse phase HPLC using a Symmetry $C_{18}$ column (100×30 mm×5 µm, 100 Å, Waters), 10 mL/min flow, solvents: A: $H_2O$ with 0.1% TFA; B: MeCN with 0.1% TFA, Instrument: Waters system with a quaternary pump, Simple Manager 2700 autoinjector, UV/Vis detector model 2487 and a Fraction collector 11, controlled by the software Masslynx version 3.5.

EXAMPLES

In the following examples L-amino acids have been used.

Example 1

Preparation of the DKP Phe(p-NH-Fmoc)-N-MePhe

The synthesis was performed in a 100 µmols scale. For the coupling of the first amino acid to the resin already modified with the Nbb handle the following protocol was used: Amino acid derivative of the first amino acid (Boc-N-MePhe-OH, 4 equiv., 400 µmols, 184.2 mg), DIPCDI (4 equiv., 400 µmols, 62 µL) and DMAP (0.4 equiv., 40 µmols, 4.9 mg) dissolved in DCM (1-3 ml/g resin) were sequentially added to the resin. The mixture was allowed to react with intermittent manual stirring for 30 min. The solvent was then removed by suction, the resin was thoroughly washed and the coupling was repeated once. Then the elimination of the Boc using TFA 40% in DCM (without doing the neutralization step) was performed. Alternatively the first amino acid can be attached as Boc-Phe-OH and then after the elimination of the Boc perform the N-alkylation on the resin using the protocol that can be divided in three steps: (a) protection and activation with O-NBS, (b) Mitsunobu reaction, (c) O-NBS removal.

The protected amino acid derivative (Boc-Phe(p-NH-Fmoc)-OH) was coupled to the first amino acid already anchored to the resin using the following protocol: Protected amino acid (Boc-Phe(p-NH-Fmoc)-OH, 5 equiv., 500 µmols, 251.3 mg) in DMF (1-3 mL/g resin) and PyAOP (5 equiv., 500 µmols, 260.2 mg) were sequentially added to the resin followed with 15 equiv. DIEA (1500 µmols, 255 µL). The mixture was left to react with intermittent manual stirring for 1 h.

The solvent was removed by filtration, the resin washed and the coupling was repeated 2 times more. The extent of the coupling was checked by the De Clercq test.

The Boc group was removed using TFA 40% in DCM (without performing the neutralization step). Finally the neutralization-cyclization and cleavage all in one step was performed by treatment of the resin with DIEA 10% in DCM 3 times during 10 min each. The filtrates were collected, DCM evaporated under $N_2$ and the residue was dissolved in $H_2O$:MeCN (1:1) and liophilized. To eliminate the salts a desalting step was performed using DOWEX MR-3 Mixed Bed resin overnight.

Product characterization: Reverse phase HPLC: linear gradient from 0 to 100% MeCN in 15 minutes using a Symmetry $C_{18}$ column (150×4.6 mm×5 µm, 100 Å, Waters), DKP Phe (ρ-NH-Fmoc)-N-MePhe $t_r$: 13.17 min. Mass spectrometry (MALDI-TOF): DKP Phe(ρ-NH-Fmoc)-N-MePhe 545.7 Da.

Example 2

Preparation of the DKP Phe(ρ-NH-Boc)-N-MePhe

The synthesis was performed in a 100 µmols scale. For the coupling of the first amino acid to the resin already modified with the Nbb handle the following protocol was used: amino acid derivative of the first amino acid (Boc-N-MePhe-OH, 4 equiv., 400 µmols, 184.2 mg), DIPCDI (4 equiv., 400 µmols, 62 µL) and DMAP (0.4 equiv., 40 µmols, 4.9 mg) dissolved in DCM (1-3 ml/g resin) were sequentially added to the resin. The mixture was allowed to react with intermittent manual stirring for 30 min. The solvent was then removed by suction, the resin was thoroughly washed and the coupling was repeated once.

Then the elimination of the Boc using TFA 40% in DCM (without doing the neutralization step) was performed. Alternatively the first amino acid can be attached as Boc-Phe-OH and then after the elimination of the Boc perform the N-alkylation on the resin using the protocol that can be divided in three steps: (a) protection and activation with O-NBS, (b) Mitsunobu reaction, (c) O-NBS removal. The protected amino acid derivative of the second amino acid was coupled to the first amino acid already anchored to the resin using the following protocol: protected amino acid (Fmoc-Phe(ρ-NH-Boc)-OH, 5 equiv., 500 µmols, 251.3 mg) in DMF (1-3 mL/g resin) and PyAOP (5 equiv., 500 µmols, 260.2 mg) were sequentially added to the resin followed with 15 equiv. DIEA (1500 µmols, 255 µL). The mixture was left to react with intermittent manual stirring for 1 h. The solvent was removed by filtration, the resin washed and the coupling was repeated 2 times more. The extent of the coupling was checked by the De Clercq test.

The Fmoc group removal and cyclization-cleavage all in one step, was performed using 20% (v/v) piperidine in DMF, 2 treatments of 10 minutes each. The filtrates were collected, DMF evaporated under reduced pressure and the residue was dissolved in $H_2O$:MeCN (1:1) and liophilized. To eliminate the salts and the remaining Fmoc byproduct the compound was purified by reverse phase HPLC using a Symmetry $C_{18}$ column (100×30 mm×5 µm, 100 Å, Waters).

Product characterization: Reverse phase HPLC: linear gradient from 0 to 100% MeCN in 15 minutes using a Symmetry $C_{18}$ column (150×4.6 mm×5 µm, 100 Å, Waters), DKP Phe (ρ-NH-Boc)-N-MePhe $t_r$: 11.04 min. Mass spectrometry (MALDI-TOF): DKP Phe(ρ-NH-Boc)-N-MePhe 424.1 Da.

Example 3

Preparation of DKP Phe(ρ-NH$_2$)—N-MePhe (compound of formula (I) with $R_1$=H; $R_2$=phenyl, $X_1$=$CH_2$, $R_3$=$CH_3$, $X_2$=NH)

The DKP Phe(ρ-NH$_2$)—N-MePhe can be easily prepared from the compounds obtained in Examples 1 or 2 by deprotection of the Boc or Fmoc group respectively in solution.

In the case of a Boc group, the Boc group was removed using TFA 50% in DCM during 1 h. Then DCM was evaporated under reduced pressure and the residue was dissolved in $H_2O$:MeCN (1:1) and liophilized.

In the case of a Fmoc group, the compound was dissolved in 1 mL of DMF and the solution at 0° C., then 50 µL of diethylamina (DEA) were added. The reaction was left to reach room temperature and stand at room temperature for 3 h under stirring. To eliminate the base and the remaining Fmoc byproduct the compound was purified by reverse phase HPLC using a Symmetry $C_{18}$ column (100×30 mm×5 µm, 100 Å, Waters).

Product characterization: Reverse phase HPLC: linear gradient from 0 to 100% MeCN in 15 minutes using a Symmetry $C_{18}$ column (150×4.6 mm×5 µm, 100 Å, Waters), DKP Phe (ρ-NH$_2$)—N-MePhe $t_r$: 6.30 min. Mass spectrometry (MALDI-TOF): DKP Phe(ρ-NH$_2$)—N-MePhe 324.1 Da. Yield (after purification): DKP Phe(ρ-NH$_2$)—N-MePhe 8%.

Example 4

Preparation of DKP N-MePhe-N-MePhe(ρ-NH$_2$) (Compound of Formula (I) with $R_1$=$CH_3$; $R_2$=phenyl, $X_1$=$CH_2$, $R_3$=$CH_3$, $X_2$=NH)

The synthesis was performed in a 100 µmols scale. For the coupling of the first amino acid to the resin already modified with the Nbb handle the following protocol was used: amino acid derivative of the first aminoacid (Fmoc-Phe(ρ-NH-Boc)-OH, 4 equiv., 400 µmols, 201 mg), DIPCDI (4 equiv., 400 µmols, 62 µL) and DMAP (0.4 equiv., 40 µmols, 4.9 mg) dissolved in DCM (1-3 ml/g resin) were sequentially added to the resin. The mixture was allowed to react with intermittent manual stirring for 30 min. The solvent was then removed by suction, the resin was thoroughly washed and the coupling was repeated once. The Fmoc group was removed with 20% (v/v) piperidine in DMF using 2 treatments of 10 minutes each. The N-alkylation of the amino acids attached to the resin was done following the protocol that can be divided in three steps: (a) Protection and activation with O-NBS: To perform the protection and activation 4 equiv. O-NBS (400 µmols, 89 mg) and 10 equiv. of collidine (1000 µmols, 132 µL) in NMP were added to the resin. The reaction was left with intermittent manual stirring for 1 h and this step was repeated once and checked by Kaiser test; (b) Mitsunobu reaction: The Mitsunobu reagents, 5 equiv. triphenylphosphine (500 µmols, 131 mg) and 10 equiv. of MeOH (1000 µmols, 24 µL) in dry THF were added to the resin and left for 1 minute, afterwars without filtering 5 equiv. of DIAD (500 µmols, 98 µL) were added in dry THF and left for another 10 minutes; (c) O-NBS removal: To proceed to the O-NBS removal 10 equiv. of α-mercaptoethanol (1000 µmols, 70 µL) and 5 equiv. of 1,8-diazabicyclo-[5.4.0]-undec-7-ene (DBU) (500 µmols, 75 µL) in NMP were added to the resin and the mixture was left to react for 5 minutes under argon atmosphere. This process was repeated once.

The protected amino acid derivative of the second amino acid was coupled to the first amino acid already anchored to the resin using the following protocol: protected amino acid (Boc-N-MePhe-OH, 5 equiv., 500 μmols, 191.9 mg) in DMF (1-3 mL/g resin) and PyAOP (5 equiv., 500 μmols, 260.2 mg) were sequentially added to the resin followed with 15 equiv. DIEA (1500 μmols, 255 μL). The mixture was left to react with intermittent manual stirring for 1 h. The solvent was removed by filtration, the resin washed and the coupling was repeated 2 times more. The extent of the coupling was checked by the De Clercq test. The Boc groups were removed using TFA 40% in DCM (without performing the neutralization step). Finally the neutralization-cyclization and cleavage all in one step was performed by treatment of the resin with DIEA 10% in DCM 3 times during 10 min each. The filtrates were collected, DCM evaporated under $N_2$ and the residue was dissolved in $H_2O$:MeCN (1:1) and liophilized. To eliminate the salts the compound was purified by reverse phase HPLC using a Symmetry $C_{18}$ column (100×30 mm×5 μm, 100 Å, Waters).

Product characterization: Reverse phase HPLC: linear gradient from 0 to 100% MeCN in 15 minutes using a Symmetry $C_{18}$ column (150×4.6 mm×5 μm, 100 Å, Waters), DKP N-MePhe-N-MePhe(ρ-$NH_2$) $t_r$: 6.39 min. Mass spectrometry (MALDI-TOF): DKP N-MePhe-N-MePhe(ρ--$NH_2$) 337.7 Da. Yield (after purification): DKP N-MePhe-N-MePhe(ρ-$NH_2$) 7.1%.

Example 5

Preparation of Compounds of Formula (II) with Z Derived from Baicalin)

The following compounds diketopiperazine DKP Phe(ρ-NH-Baicalin)-N-MeX where X: phenylalanine (Phe) (5a), cyclohexylalanine (Cha) (5b), 2-naphtylalanine (2NaI) (5c), 1-pyrenylalanine (1PyrenylAla) (5d), homophenylalanine (HomoPhe) (5e), and 2-amino-octanoic acid (Oct) (5f) have been prepared using the same methodology.

TABLE 2

Examples of compounds of formula (II)

| | $R_1$ | $R_2$ | $R_3$ | $X_2$ | $X_1$ |
|---|---|---|---|---|---|
| 5a | H | phenyl | $CH_3$ | NH | $CH_2$ |
| 5b | H | cyclohexyl | $CH_3$ | NH | $CH_2$ |
| 5c | H | 2-naphtyl | $CH_3$ | NH | $CH_2$ |
| 5d | H | pyrenyl | $CH_3$ | NH | $CH_2$ |
| 5e | H | phenyl | $CH_3$ | NH | $CH_2$—$CH_2$ |
| 5f | H | H | $CH_3$ | NH | $(CH_2)_6$ |

The syntheses were performed in a 100 μmols scale/each. For the coupling of the first amino acid to the resin already modified with the Nbb handle the following protocol was used: amino acid derivative of the first amino acid (Boc-X—OH or Fmoc-X—OH, 4 equiv., 400 μmols, Boc-Phe-OH 106.1 mg, Boc-HomoPhe-OH 111.7 mg, Boc-Cha-OH 108.6 mg, Boc-Oct-OH 103.7 mg, Fmoc-2NaI-OH 175 mg, Fmoc-1PyrenylAla-OH 204.6 mg), DIPCDI (4 equiv., 400 μmols, 62 μL) and DMAP (0.4 equiv., 40 μmols, 4.9 mg) dissolved in DCM (1-3 ml/g resin) were sequentially added to the resin. The mixture was allowed to react with intermittent manual stirring for 30 min. The solvent was then removed by suction, the resin was thoroughly washed and the coupling was repeated once. Then the elimination of the Boc or Fmoc group was performed using TFA 40% in DCM (without performing the neutralization step) or 20% (v/v) piperidine in DMF using 2 treatments of 10 minutes each for the removal of the Fmoc group. The N-alkylation of the amino acids attached to the resin was done following the protocol that can be divided in three steps: (a) Protection and activation with O-NBS: To perform the protection and activation 4 equiv. O-NBS (400 μmols, 89 mg) and 10 equiv. of collidine (1000 μmols, 132 μL) in NMP were added to the resin. The reaction was left with intermittent manual stirring for 1 h and this step was repeated once and checked by Kaiser test; (b) Mitsunobu reaction: The Mitsunobu reagents, 5 equiv. triphenylphosphine (500 μmols, 131 mg) and 10 equiv. MeOH (1000 μmols, 24 μL) in dry THF were added to the resin and left for 1 minute, afterwars without filtering 5 equiv. of DIAD (500 μmols, 98 μL) were added in dry THF and left for another 10 minutes; (c) O-NBS removal: To proceed to the O-NBS removal 10 equiv. of β-mercaptoethanol (1000 μmols, 70 μL) and 5 equiv. of DBU (500 μmols, 75 μL) in NMP were added to the resin and the mixture was left to react for 5 minutes under argon atmosphere. This process was repeated once.

The protected amino acid derivative of the second amino acid was coupled to the first amino acid already anchored to the resin using the following protocol.

Protected amino acid (Boc-Phe(ρ-NH-Fmoc)-OH, 5 equiv., 500 μmols, 260.3 mg) in DMF (1-3 mL/g resin) and PyAOP (5 equiv., 500 μmols, 260.2 mg) were sequentially added to the resin followed with 15 equiv. DIEA (1500 μmols, 255 μL). The mixture was left to react with intermittent manual stirring for 1 h. The solvent was removed by filtration, the resin washed and the coupling was repeated 2 times more. The extent of the coupling was checked by the De Clercq test. The Fmoc group was removed using 20% (v/v) piperidine in DMF, 2 treatments of 10 minutes each were used for the removal of the Fmoc group. Coupling of the cargo with a COOH moiety (e.g. Baicalin) to the amino group: For the coupling of the cargo to the BBB-shuttle anchored on the resin the following protocol was used: Cargo-COOH (Baicalin) (5 equiv., 500 μmols, 224 mg) in DMF (1-3 mL/g resin), PyBOP (5 equiv., 500 μmols, 260.2 mg) and HOAt (15 equiv., 1500 μmols, 196 mg) were sequentially added to the resin followed with 15 equiv. DIEA (1500 μmols, 255 μL). The mixture was left to react with intermittent manual stirring for 2 h. The solvent was removed by filtration, the resin washed and the coupling was repeated once. The extent of the coupling was checked by the Kaiser test. The Boc group was removed using TFA 40% in DCM (without doing the neutralization step). Finally the neutralization-cyclization and cleavage all in one step was performed by treatment of the resin with DIEA 10% in DCM 3 times during 10 min each. The filtrates were collected, DCM evaporated under $N_2$ and the residue is dissolved in $H_2O$:MeCN (1:1) and liophilized. The product was purified if necessary.

Product characterization: Reverse phase HPLC: linear gradient from 0 to 100% MeCN in 15 minutes using a Symmetry $C_{18}$ column (150×4.6 mm×5 μm, 100 Å, Waters), compound 5a $t_r$: 9.30 min, compound 5b $t_r$: 8.65 min, compound 5c $t_r$: 9.48 min, compound 5d $t_r$: 9.50 min, compound 5e $t_r$: 8.87 min, compound 5f $t_r$: 10.47 min. (Confirmed by HPLC-MS). Mass spectrometry (MALDI-TOF): compound 5a: 752.2 Da, compound 5b: 758.1 Da, compound 5c: 801.4 Da, compound 5d: 876.3 Da, compound 5e: 766.1 Da, compound 5f: 745.4 Da. Yield (after purification): compound 5a: 1.2%, compound 5b: 2.4%, compound 5c: 2.5%, compound 5d: 1.4%, compound 5e: 1.7%, compound 5f: 1.1%.

Example 6

Preparation of Compounds of Formula (II) with Z Derived from Dopamine

The following compounds DKP Phe(ρ-NH—$CH_2$—CO-Dopamine)-N-MeX where X: phenylalanine (Phe) (6a), cyclohexylalanine (Cha) (6b), 2-naphtylalanine (2NaI) (6c), 1-Pyrenylalanine (1PyrenylAla) (6d), homophenylalanine (HomoPhe) (6e), and 2-amino-octanoic acid (Oct) (6f), have been prepared using the same methodology.

TABLE 3

Examples of compounds of formula (II)

|    | $R_1$ | $R_2$     | $R_3$  | $X_2$              | $X_1$         |
|----|-------|-----------|--------|--------------------|---------------|
| 6a | H     | phenyl    | $CH_3$ | $NH-(CH_2)-CO$     | $CH_2$        |
| 6b | H     | cyclohexyl| $CH_3$ | NH                 | $CH_2$        |
| 6c | H     | 2-naphtyl | $CH_3$ | NH                 | $CH_2$        |
| 6d | H     | pyrenyl   | $CH_3$ | NH                 | $CH_2$        |
| 6e | H     | phenyl    | $CH_3$ | NH                 | $CH_2-CH_2$   |
| 6f | H     | H         | $CH_3$ | NH                 | $(CH_2)_6$    |

The syntheses were performed in a 100 μmols scale/each. For the coupling of the first amino acid to the resin already modified with the Nbb handle the following protocol was used: amino acid derivative of the first amino acid (Boc-X—OH or Fmoc-X—OH, 4 equiv., 400 μmols, Boc-Phe-OH 106.1 mg, Boc-HomoPhe-OH 111.7 mg, Boc-Cha-OH 108.6 mg, Boc-Oct-OH 103.7 mg, Fmoc-2NaI-OH 175 mg, Fmoc-1PyrenylAla-OH 204.6 mg), DIPCDI (4 equiv., 400 μmols, 62 μL) and DMAP (0.4 equiv., 40 μmols, 4.9 mg) dissolved in DCM (1-3 ml/g resin) were sequentially added to the resin. The mixture was allowed to react with intermittent manual stirring for 30 min. The solvent was then removed by suction, the resin was thoroughly washed and the coupling was repeated once. Then the elimination of the Boc or Fmoc group was performed using TFA 40% in DCM (without performing the neutralization step) or 20% (v/v) piperidine in DMF using 2 treatments of 10 minutes each for the removal of the Fmoc group. The N-alkylation of the amino acids attached to the resin was done following the protocol that can be divided in three steps: (a) Protection and activation with O-NBS: To perform the protection and activation 4 equiv. O-NBS (400 μmols, 89 mg) and 10 equiv. of collidine (1000 μmols, 132 μL) in NMP were added to the resin. The reaction was left with intermittent manual stirring for 1 h and this step was repeated once and checked by Kaiser test; (b) Mitsunobu reaction: The Mitsunobu reagents, 5 equiv. triphenylphosphine (500 μmols, 131 mg) and 10 equiv. of MeOH (1000 μmols, 24 μL) in dry THF were added to the resin and left for 1 minute, afterwards without filtering 5 equiv. of DIAD (500 μmols, 98 μL) were added in dry THF and left for another 10 minutes; (c) O-NBS removal: To proceed to the O-NBS removal 10 equiv. of β-mercaptoethanol (1000 μmols, 70 μL) and 5 equiv. of DBU (500 μmols, 75 μL) in NMP were added to the resin and the mixture was left to react for 5 minutes under argon atmosphere. This process was repeated once.

The protected amino acid derivative of the second amino acid was coupled to the first amino acid already anchored to the resin using the following protocol. Protected amino acid (Boc-Phe(ρ-NH-Fmoc)-OH, 5 equiv., 500 μmols, 260.3 mg) in DMF (1-3 mL/g resin) and PyAOP (5 equiv., 500 μmols, 260.2 mg) were sequentially added to the resin followed with 15 equiv. DIEA (1500 μmols, 255 μL). The mixture was left to react with intermittent manual stirring for 1 h. The solvent was removed by filtration, the resin washed and the coupling was repeated 2 times more. The extent of the coupling was checked by the De Clercq test. The Fmoc group was removed using 20% (v/v) piperidine in DMF, 2 treatments of 10 minutes each were used for the removal of the Fmoc group. The introduction of the cargo anchoring moiety was done by reductive amination. This process was done using the following protocol: Glyoxylic acid (H—CO—COOH) (5 equiv., 500 μmols, 37 mg) in DMF with 1% AcOH (1-3 mL/g resin), was added to the resin and the mixture was left to react with intermittent manual stirring for 30 min. The solvent was removed by filtration and the resin washed. Then $NaBH_3CN$ (3 equiv., 300 μmols, 18.8 mg) in DMF with 1% AcOH were added to the resin and left to react during 1 h. The solvent was removed by filtration and the resin washed. The coupling of the cargo with a $NH_2$ moiety (e.g. dopamine) to the carboxylic acid anchoring moiety was done in two steps: First the carboxylic group was activated with DIPCDI (5 equiv., 500 μmols, 78 μL) and HOAt (5 equiv., 500 μmols, 68 mg) in DMF for 30 min, after which the solvent was removed by suction and the resin was washed. The coupling was performed using 5 equiv. $NH_2$-Cargo (dopamine) (5 equiv., 500 μmols, 98 mg) in DMF. The mixture is left to react overnight. The solvent was removed by filtration, the resin washed.

The Boc group was removed using TFA 40% in DCM (without doing the neutralization step). Finally the neutralization-cyclization and cleavage all in one step was performed by treatment of the resin with DIEA 10% in DCM 3 times during 10 min each. The filtrates were collected, DCM evaporated under $N_2$ and the residue is dissolved in $H_2O$: MeCN (1:1) and liophilized. The product was purified if necessary.

Product characterization: Reverse phase HPLC: linear gradient from 15 to 65% MeCN in 15 minutes using a Symmetry $C_{18}$ column (150×4.6 mm×5 μm, 100 Å, Waters), compound 6a $t_r$: 7.83 min, compound 6b $t_r$: 9.36 min, compound 6c $t_r$: 9.61 min, compound 6d $t_r$: 11.75 min, compound 6e $t_r$: 7.85 min, compound 6f $t_r$: 10.58 min. (Confirmed by HPLC-MS). Mass spectrometry (HPLC-MS): compound 6a: 516.5 Da, compound 6b: 522.5 Da, compound 6c: 566.2 Da, compound 6d: 640.4 Da, compound 6e: 530.3 Da, compound 6f: 510.4 Da. Yield (after purification): compound 6a: 10.8%, compound 6b: 7.2%, compound 6c: 10.9%, compound 6d: 9.6%, compound 6e: 9.1%, compound 6f: 8.2%.

Example 7

Preparation of the DKP Phe(ρ-NH—$CH_2$—COOH)—N-MePhe (Compound of Formula (I) with $R_1$=H; $R_2$=phenyl, $X_1$=$CH_2$, $R_3$=$CH_3$, $X_2$=$NHCH_2COO$)

The synthesis was performed in a 100 μmols scale. For the coupling of the first amino acid to the resin already modified with the Nbb handle the following protocol was used: amino acid derivative 4 equiv., 400 μmols, Boc-Phe-OH 106.1 mg, DIPCDI (4 equiv., 400 μmols, 62 μL) and DMAP (0.4 equiv., 40 μmols, 4.9 mg) dissolved in DCM (1-3 ml/g resin) were sequentially added to the resin. The mixture was allowed to react with intermittent manual stirring for 30 min. The solvent was then removed by suction, the resin was thoroughly washed and the coupling was repeated once. Then the elimination of the Boc was performed using TFA 40% in DCM (without performing the neutralization step). The N-alkylation of the amino acid attached to the resin was done following the protocol that can be divided in three steps: (a) protection and activation with O-NBS: To perform the protection and activation 4 equiv. O-NBS (400 μmols, 89 mg) and 10 equiv. of collidine (1000 μmols, 132 μL) in NMP were added to the resin. The reaction was left with intermittent manual stirring for 1 h and this step was repeated once and checked by Kaiser test. (b) Mitsunobu reaction: The Mitsunobu reagents, 5 equiv. triphenylphosphine (500 μmols, 131 mg) and 10 equiv. of MeOH (1000 μmols, 24 μL) in dry THF were added to the resin and left for 1 minute, afterwars without filtering 5 equiv. of DIAD (500 µmols, 98 µL) were added in dry THF and left for another minutes. (c) O-NBS removal: To proceed to the O-NBS removal 10 equiv. of β-mercaptoethanol (1000 µmols, 70 µL) and 5 equiv. of DBU (500 µmols, 75 µL) in NMP were added to the resin and the mixture was left to react for 5 minutes under argon atmosphere. This process was repeated once.

The protected amino acid derivative of the second amino acid was coupled to the first amino acid already anchored to the resin using the following protocol. Protected amino acid (Boc-Phe(ρ-NH-Fmoc)-OH, 5 equiv., 500 µmols, 260.3 mg) in DMF (1-3 mL/g resin) and PyAOP (5 equiv., 500 µmols, 260.2 mg) were sequentially added to the resin followed with 15 equiv. DIEA (1500 µmols, 255 µL). The mixture was left to react with intermittent manual stirring for 1 h. The solvent was removed by filtration, the resin washed and the coupling was repeated 2 times more. The extent of the coupling was checked by the De Clercq test. The Fmoc group was removed using 20% (v/v) piperidine in DMF, 2 treatments of 10 minutes each were used for the removal of the Fmoc group. The introduction of the cargo anchoring moiety was done by reductive amination. This process was done using the following protocol: Glyoxylic acid (H—CO—COOH) (5 equiv., 500 µmols, 37 mg) in DMF with 1% AcOH (1-3 mL/g resin), was added to the resin and the mixture was left to react with intermittent manual stirring for 30 min. The solvent was removed by filtration and the resin washed. Then NaBH$_3$CN (3 equiv., 300 µmols, 18.8 mg) in DMF with 1% AcOH were added to the resin and left to react during 1 h. The solvent was removed by filtration and the resin washed. The carboxylic acid was modified with a methyl ester in two steps: First the carboxylic group was activated with DIPCDI (5 equiv., 500 µmols, 78 µL) and HOAt (5 equiv., 500 µmols, 68 mg) in DMF for 30 min, after which the solvent was removed by suction and the resin was washed. The coupling was performed using 5 equiv. MeOH (500 µmols, 8 µL) in DMF. The mixture is left to react overnight. The solvent was removed by filtration, the resin washed. The Boc group was removed using TFA 40% in DCM (without doing the neutralization step). Finally the neutralization-cyclization and cleavage all in one step was performed by treatment of the resin with DIEA 10% in DCM 3 times during 10 min each. The filtrates were collected, DCM evaporated under N$_2$ and the residue is dissolved in H$_2$O:MeCN (1:1) and liophilized. Afterwards the methyl ester was hydrolized with 1.5 equiv. LiOH (150 µmols, 6.3 mg) in H$_2$O:MeOH (1:1) stirring at room temperature during 30 min. Then the solution is acidified and liophilized. The product was purified.

Product characterization: Reverse phase HPLC: linear gradient from 0 to 100% MeCN in 15 minutes using a Symmetry C$_{18}$ column (150×4.6 mm×5 µm, 100 Å, Waters), DKP Phe (ρ-NH—CH$_2$—COOH)—N-MePhe t$_r$: 7.86 min (Confirmed by HPLC-MS). Mass spectrometry (HPLC-MS): DKP Phe (ρ-NH—CH$_2$—COOH)—N-MePhe 381.0 Da. Yield (after purification): DKP Phe(ρ-NH—CH$_2$—COOH)—N-MePhe 13%.

Example 8

BBB Transport Evaluation Techniques

Parallel artificial membrane permeability assay (PAMPA). The evaluation method chosen is the Parallel Artificial Membrane Permeability Assay (PAMPA), which allows to predict or evaluate only this transport mechanism. In general terms, this method is simple, automatizable with high throughput, has a low cost and require only a small amount of test compound. The PAMPA method originally introduced by Kansy at Roche uses an artificial membrane in the form of filter supported phospholipids bilayers (cf. M. Kansy et al., "Physicochemical high throughput screening: Parallel artificial membrane permeability assay in the description of the absorption processes" *J. Med. Chem.* 1998, vol. 41, pp. 1007-1010). The phospholipid membrane mimics the cell membrane, but has no means for active or paracellular transport of drug molecules. It is a very convenient tool to evaluate the transport of compounds by passive diffusion. This technique allows the evaluation of pure compounds, crudes or even mixtures of compounds.

PAMPA assay is used to determine the ability of the BBB shuttle-cargo constructs to cross the BBB by passive diffusion. The effective permeability of the compounds was measured by triplicate at a initial concentration of 200 µM. The buffer solution was prepared from the concentrated one commercialized by pION following their indications. pH was adjusted to 7.4 using a NaOH 0.5M solution. The compound of interest was dissolved to the desired concentration (200 µM).

The PAMPA sandwich was separated and the donor well was filled with 200 µL of the compound solution to be studied. The acceptor plate was placed into the donor plate making sure that the underside of membrane was in contact with buffer. 4 µL of mixture of phospholipids (20 mg/mL) in dodecane were added into each well and 200 µL of buffer solution were added to the each acceptor well. The plate was covered and incubated at room temperature in a saturated humidity atmosphere for 4 hours under orbital agitation at 100 rpm. After the 4 hours, 150 µL/well from the donor plate and 150 µL/well from the acceptor plate were transferred to HPLC vials and 100 µL/each sample were injected in a HPLC reverse phase column, Symmetry C$_{18}$ column (150×4.6 mm×5 µm, 100 Å, Waters). The transport was also confirmed by MALDI-TOF spectrometry and HPLC-MS of aliquotes of the acceptor wells. The mixture of phospholipids used is a porcine polar brain lipid extract. Composition: phosphatidylcholine (PC) 12.6%, phosphatidylethanolamine (PE) 33.1%, phosphatidylserine (PS) 18.5%, phosphatidylinositol (PI) 4.1%, phosphatidic acid 0.8% and 30.9% of other compounds. The effective permeability was calculated using the following equation:

$$P_e = \frac{-218.3}{t} \cdot \text{Log}\left[1 - \frac{2 \cdot C_A(t)}{C_D(t_0)}\right] \cdot 10^{-6} \text{ cm/s}$$

where:
t time (hours)
$C_A(t)$ Compound concentration at the acceptor well at time t
$C_D(t_0)$ Compound concentration at the donor well at 0 h As a control, the transport of propranolol was evaluated in parallel and a mass balance was calculated for all the studied compounds in order to detect if retention in the phospholipids occur.

The different compounds were evaluated by PAMPA assay. PAMPA assay only measures the transport by passive diffusion, so the positive transport measured for these compounds shows that these compounds have a positive transport across the BBB in vivo by passive diffusion.

One must take into account that probably the optimal BBB-shuttle may variate depending on the cargo attached.

In the Tables 4 and 5, one can see how the use of the BBB-shuttle-cargo constructs allowed that cargoes that do not cross by themselves, such as baicalin and dopamine, can now cross the membrane by passive diffusion.

TABLE 4

Effective permeability ($P_e$) found in the PAMPA assay for the Phe(p-NH—CO-Baicalin)-N-MePhe, Phe(p-NH—CO-Baicalin)-N-MeCha, Phe(p-NH—CO-Baicalin)-N-Me2NaI, Phe(p-NH—CO-Baicalin)-N-Me1PyrenylAla, Phe(p-NH—CO-Baicalin)-N-MeHomoPhe, Phe(p-NH—CO-Baicalin)-N-MeOct (BBB-shuttle-cargo construct) and Baicalin (Cargo).

| Compound | $P_e$ (cm/s) | Log $P_e$ |
|---|---|---|
| Baicalin | —* | —* |
| DKP Phe(p-NH—CO-baicalin)-N-MePhe (5a) | $1.33\ 10^{-8}$ | −7.7 |
| DKP Phe(p-NH—CO-baicalin)-N-MeCha (5b) | $3.65\ 10^{-7}$ | −6.4 |
| DKP Phe(p-NH—CO-baicalin)-N-Me2NaI (5c) | $3.70\ 10^{-6}$ | −5.4 |
| DKP Phe(p-NH—CO-baicalin)-N-Me1PyrenylAla (5d) | $0.19\ 10^{-8}$ | −8.7 |
| DKP Phe(p-NH—CO-baicalin)-N-MeHomoPhe (5e) | $0.05\ 10^{-8}$ | −9.3 |
| DKP Phe(p-NH—CO-baicalin)-N-MeOct (5f) | $4.97\ 10^{-7}$ | −6.3 |

*Baicalin was not detected in the acceptor well of the PAMPA assay after 4 h.

TABLE 5

Effective permeability ($P_e$) found in the PAMPA assay for the DKP Phe(p-NH—CH$_2$—CO-NH-Dopamine)-N-MePhe, DKP Phe(p-NH—CH$_2$—CO—NH-Dopamine)-N-MeCha, DKP Phe(p-NH—CH$_2$—CO—NH-Dopamine)-N-Me2NaI, DKP Phe(p-NH—CH$_2$—CO—NH-Dopamine)-N-Me(1PyrenylAla), DKP Phe(p-NH—CH$_2$—CO—NH-Dopamine)-N-MeHomoPhe, DKP Phe(p-NH—CH$_2$—CO—NH-Dopamine)-N-MeOct and Dopamine (Cargo) and L-Dopa (Current drug used in the market).

| Compound | Pe (cm/s) | Log Pe |
|---|---|---|
| Dopamine | —* | —* |
| L-Dopa | —* | —* |
| DKP Phe(p-NH—CH$_2$—CO—NH-dopamine)-N-MePhe (6a) | $3.61\ 10^{-8}$ | −7.4 |
| DKP Phe(p-NH—CH$_2$—CO—NH-dopamine)-N-MeCha (6b) | $2.28\ 10^{-8}$ | −7.6 |
| DKP Phe(p-NH—CH$_2$—CO—NH-dopamine)-N-Me2NaI (6c) | $11.5\ 10^{-8}$ | −6.9 |
| DKP Phe(p-NH—CH$_2$—CO—NH-dopamine)-N-Me(1PyrenylAla) (6d) | $1.90\ 10^{-8}$ | −7.7 |
| DKP Phe(p-NH—CH$_2$—CO—NH-dopamine)-N-MeHomoPhe (6e) | $0.76\ 10^{-8}$ | −8.1 |
| DKP Phe(p-NH—CH$_2$—CO—NH-dopamine)-N-MeOct (6f) | $32.1\ 10^{-8}$ | −6.5 |

*These compounds were not detected in the acceptor well of the PAMPA assay after 4 h.

Dopamine and baicalin are difficult cargoes that can not cross the BBB by passive diffusion at all. The BBB-shuttle-cargo constructs based on N-MeOct and N-Me2NaI have been the most optimal to cross cargos as dopamine and baicalin.

Immobilized Artificial Membrane Chromatography:

To evaluate the BBB-shuttles and BBB-shuttle-cargo constructs, a chromatographic technique, IAMC (immobilized artificial membrane chromatography) developed by Pidgeon was used (cf. A. Albert, Chemical aspects of selective toxicity. *Nature* 1958, vol. 182, pp. 421-423). This technique uses phospholipid molecules covalently immobilized to silica particles at high density as the stationary phase. It has been used to purify membrane proteins, to immobilize enzymes and to predict transport across biological barriers. It exhibits a good correlation with in vitro cell based assays and it is very convenient in terms of high throughput. IAMC interactions include ionic, lipophilic and hydrogen bonding interactions that can be combined under a parameter known as phospholipophilicity.

Retention times were determined using an IAMC column with phosphatidylcholine (PC), the major phospholipid found in cell membranes, covalently immobilized (10×4.6 mm, 12 μm, 300 Å, IAM.PC.DD2 column, Regis Technologies Inc.). The compounds were detected by UV absorption at 220 nm. The chromatograms were obtained using an HPLC working isocratically with a mobile phase containing 10 mM phosphate buffer, 2.7 mM KCl and 137 mM NaCl at pH 7.4 and 20% MeCN (flow 0.5 mL/min). The retention times ($t_r$) were transformed into capacity factors ($k_{IAM}$) according to the following equation: $k_{IAM}=(t_r-t_0)/t_0$, where $t_r$ is the retention time of the studied compound and $t_0$ is the retention time of a compound that would not be retained by the column (e.g. citric acid). As a control, propranolol was studied.

BBB-shuttles and the BBB-shuttle-cargo constructs were also evaluated by IAMC (Immobilized Artificial Membrane Chromatography), a chromatographic technique that measures the phospholipophilicity of our compounds, their tendency to interact with phosphatidylcholine covalently immobilized. See results in Table 6 and 7.

IAMC showed that BBB-shuttle constructs with baicalin exhibited improved $k_{IAM}$ values (Table 6) and the same occurred in the case of dopamine based BBB-shuttle-cargo constructs (Table 7). These compounds show better phospholipophilicity, reaching high capacity factors ($k_{IAM}$).

TABLE 6

Capacity factors ($k_{IAM}$) found in the IAMC assay for the Phe(p-NH—CO-Baicalin)-N-MePhe, Phe(p-NH—CO-Baicalin)-N-MeCha, Phe(p-NH—CO-Baicalin)-N-Me2NaI, Phe(p-NH—CO-Baicalin)-N-Me1PyrenylAla, Phe(p-NH—CO-Baicalin)-N-MeHomoPhe, Phe(p-NH—CO-Baicalin)-N-MeOct (BBB-shuttle-cargo constructs) and Baicalin (Cargo).

| Compound | $k_{IAM}$ |
|---|---|
| Baicalin | 1.24 |
| DKP Phe(p-NH—CO-baicalin)-N-MePhe (5a) | 2.42 |
| DKP Phe(p-NH—CO-baicalin)-N-MeCha (5b) | 6.09 |
| DKP Phe(p-NH—CO-baicalin)-N-Me2NaI (5c) | 10.66 |
| DKP Phe(p-NH—CO-baicalin)-N-Me(1PyrenylAla) (5d) | >100 |
| DKP Phe(p-NH—CO-baicalin)-N-MeHomoPhe (5e) | 4.15 |
| DKP Phe(p-NH—CO-baicalin)-N-MeOct (5f) | 10.47 |

TABLE 7

Capacity factors ($k_{IAM}$) found in the IAMC assay for the DKP Phe(p-NH—CH$_2$—CO—NH-Dopamine)-N-MePhe, DKP Phe(p-NH—CH$_2$—CO—NH-Dopamine)-N-MeCha, DKP Phe(p-NH—CH$_2$—CO—NH-Dopamine)-N-Me2NaI, DKP Phe(p-NH—CH$_2$—CO—NH-Dopamine)-N-Me(1PyrenylAla), DKP Phe(p-NH—CH$_2$—CO—NH-Dopamine)-N-MeHomoPhe, DKP Phe(p-NH—CH$_2$—CO—NH-Dopamine)-N-MeOct and Dopamine (Cargo).

| Compound | $k_{IAM}$ |
|---|---|
| Dopamine | 0.30 |
| DKP Phe(p-NH—CH$_2$—CO—NH-dopamine)-N-MePhe (6a) | 3.54 |
| DKP Phe(p-NH—CH$_2$—CO—NH-dopamine)-N-MeCha (6b) | 0.86 |
| DKP Phe(p-NH—CH$_2$—CO—NH-dopamine)-N-Me2NaI (6c) | 16.14 |
| DKP Phe(p-NH—CH$_2$—CO—NH-dopamine)-N-Me(1PyrenylAla) (6d) | >100 |
| DKP Phe(p-NH—CH$_2$—CO—NH-dopamine)-N-MeHomoPhe (6e) | 3.15 |
| DKP Phe(p-NH—CH$_2$—CO—NH-dopamine)-N-MeOct (6f) | 15.47 |

The invention claimed is:

1. A compound of formula (I), or a pharmaceutically acceptable salt thereof, including any stereoisomer or mixtures of stereoisomers,

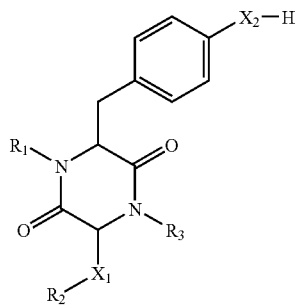

wherein:
R₁ and R₃ are radicals independently selected from the group consisting of H and (C₁-C₄)-alkyl, wherein either R₁ or R₃ is methyl; or alternatively, R₁ and R₃ are both methyl; R₂ is phenyl, cyclohexyl, 2-napthtyl, or 1-pyrenyl;
X₁ is —CH₂ or CH₂—CH₂; and
X₂ is a biradical selected from the group consisting of —NH—, —NH—(CH₂)₁₋₃—COO—, —NH—(CH₂)₁₋₃—S—, and —NH—CO—(CH₂)₁₋₃—S—.

2. The compound according to claim 1 which is selected from the group consisting of: the compound of formula (I) with R₁=H; R₂=phenyl, X₁=CH₂, R₃=CH₃, and X₂=NH, the compound of formula (I) with R₁=CH₃; R₂=phenyl, X₁=CH₂, R₃=CH₃, and X₂=NH, and the compound of formula (I) with R₁=H; R₂=phenyl, X₁=CH₂, R₃=CH₃, and X₂=NHCH₂COO.

3. The compound according to claim 1, wherein R₁ is methyl.

4. The compound according to claim 1, wherein R₃ is methyl.

5. The compound according to claim 1, wherein R₁ and R₃ are methyl.

6. The compound according to claim 1 where R₁=H; R₂=phenyl, X₁=CH₂, R₃=CH₃, and X₂=NH.

7. The compound according to claim 1 where R₁=CH₃; R₂=phenyl, X₁=CH₂, R₃=CH₃, and X₂=NH.

8. The compound according to claim 1 where R₁=H; R₂=phenyl, X₁=CH₂, R₃=CH₃, and X₂=NHCH₂COO.

9. The compound according to claim 1 where R₁=H; R₂=phenyl, X₁=CH₂—CH₂, R₃=CH₃, and X₂=NH.

* * * * *